(12) United States Patent
Shimamoto et al.

(10) Patent No.: US 10,606,067 B2
(45) Date of Patent: Mar. 31, 2020

(54) DRIVE-CONDITION SETTING DEVICE AND DRIVE-CONDITION SETTING METHOD FOR OPTICAL SCANNING APPARATUS

(71) Applicant: OLYMPUS CORPORATION, Tokyo (JP)

(72) Inventors: Atsuyoshi Shimamoto, Tokyo (JP); Masashi Yamada, Tokyo (JP); Soichiro Koshika, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 105 days.

(21) Appl. No.: 15/839,177

(22) Filed: Dec. 12, 2017

(65) Prior Publication Data

US 2018/0113298 A1 Apr. 26, 2018

Related U.S. Application Data

(63) Continuation of application No. PCT/JP2015/068000, filed on Jun. 23, 2015.

(51) Int. Cl.
*G02B 26/10* (2006.01)
*A61B 1/00* (2006.01)
(Continued)

(52) U.S. Cl.
CPC ........ *G02B 26/101* (2013.01); *A61B 1/00006* (2013.01); *A61B 1/00172* (2013.01);
(Continued)

(58) Field of Classification Search
CPC .............. G02B 26/101; G02B 23/2469; G02B 26/103; G11B 15/026; A61B 1/00006; A61B 1/00172; A61B 1/00045
(Continued)

(56) References Cited

U.S. PATENT DOCUMENTS

| 6,845,190 B1 * | 1/2005 | Smithwick | ........... A61B 1/0008 385/1 |
|---|---|---|---|
| 7,129,472 B1 * | 10/2006 | Okawa | ............... A61B 1/00059 250/234 |

(Continued)

FOREIGN PATENT DOCUMENTS

| EP | 1142529 A1 | 10/2001 |
|---|---|---|
| EP | 2742848 A1 | 6/2014 |

(Continued)

OTHER PUBLICATIONS

WIPO Translation into English of JP 2014-198089 A, from https://patentscope.wipo.int; performed Jun. 21, 2019.*

(Continued)

*Primary Examiner* — Jennifer D. Carruth
(74) *Attorney, Agent, or Firm* — Scully, Scott, Murphy & Presser, P.C.

(57) ABSTRACT

A drive-condition setting device applied to an optical scanning apparatus having a fiber and an actuator that vibrates a distal end of the fiber, the drive-condition setting device detects a scan pattern of the illumination light output from the fiber, measures resonance frequencies in the x direction and the y direction of the fiber, sets a drive frequency and a drive voltage based on the resonance frequencies such that conditional expressions below are satisfied: when $fx>fy$, $fd<fy$ and $Vx \geq Vy$ (1) or $fd>fx$ and $Vx \leq Vy$ (2), and when $fx \leq fy$, $fd<fx$ and $Vx \leq Vy$ (3) or $fd>fy$ and $Vx \geq Vy$ (4) where fd denotes the drive frequency, Vx denotes a maximum voltage of a X direction drive signal, and Vy denotes a maximum voltage of a y direction drive signal.

3 Claims, 8 Drawing Sheets

(51) Int. Cl.
 *G02B 23/24* (2006.01)
 *G11B 15/02* (2006.01)
(52) U.S. Cl.
 CPC ....... *G02B 23/2469* (2013.01); *G02B 26/103* (2013.01); *G11B 15/026* (2013.01)
(58) Field of Classification Search
 USPC ............ 359/202.1, 203.1, 209.1, 221.2
 See application file for complete search history.

(56) References Cited

U.S. PATENT DOCUMENTS

| | | | | |
|---|---|---|---|---|
| 9,219,221 | B2* | 12/2015 | Funakubo | H01L 41/047 |
| 9,612,435 | B2* | 4/2017 | Shimamoto | G02B 21/0044 |
| 9,993,139 | B2* | 6/2018 | Shimamoto | A61B 1/00006 |
| 10,151,916 | B2* | 12/2018 | Mori | A61B 1/07 |
| 2004/0122328 | A1* | 6/2004 | Wang | A61B 1/00048 |
| | | | | 600/476 |
| 2006/0013528 | A1* | 1/2006 | Rosman | B82Y 35/00 |
| | | | | 385/25 |
| 2006/0072843 | A1* | 4/2006 | Johnston | G06K 9/20 |
| | | | | 382/254 |
| 2008/0291597 | A1 | 11/2008 | Seibel et al. | |
| 2009/0015894 | A1* | 1/2009 | Rosman | A61B 5/0062 |
| | | | | 359/199.1 |
| 2009/0028407 | A1* | 1/2009 | Seibel | A61B 1/0008 |
| | | | | 382/131 |
| 2009/0092364 | A1* | 4/2009 | Johnston | A61B 1/00096 |
| | | | | 385/117 |
| 2009/0316116 | A1* | 12/2009 | Melville | A61B 1/0008 |
| | | | | 353/31 |
| 2013/0242069 | A1* | 9/2013 | Kobayashi | A61B 1/00009 |
| | | | | 348/65 |
| 2014/0194692 | A1 | 7/2014 | Yoshino et al. | |

FOREIGN PATENT DOCUMENTS

| | | |
|---|---|---|
| JP | 2001-174744 A | 6/2001 |
| JP | 2008-514344 A | 5/2008 |
| JP | 2010-527688 A | 8/2010 |
| JP | 5190267 B2 | 4/2013 |
| JP | 2014-44265 A | 3/2014 |
| JP | 2014-145941 A | 8/2014 |
| JP | 2014-147462 A | 8/2014 |
| JP | 2014-198089 A | 10/2014 |
| WO | WO 2006/041452 A1 | 4/2006 |
| WO | WO 2006/041459 A1 | 4/2006 |
| WO | WO 2008/143623 A1 | 11/2008 |
| WO | WO 2013/069382 A1 | 5/2013 |

OTHER PUBLICATIONS

International Search Report dated Sep. 29, 2015 issued in PCT/JP2015/068000.

* cited by examiner

DRIVE-CONDITION SETTING DEVICE AND DRIVE-CONDITION SETTING METHOD FOR OPTICAL SCANNING APPARATUS

CROSS-REFERENCE TO RELATED APPLICATIONS

This application is a Continuation Application of International Application No. PCT/JP2015/068000 filed on Jun. 23, 2015. The content of International Application No. PCT/JP2015/068000 is hereby incorporated herein by reference in its entirety.

TECHNICAL FIELD

The present invention relates to drive-condition setting devices and drive-condition setting methods.

BACKGROUND ART

An optical scanning apparatus that vibrates the distal end of a fiber, which optically guides light emitted from a light source, to make the output light from the fiber scan an observation target such that the pattern of the output light forms a spiral shape, thus performing a so-called spiral scan, has been proposed.

In such an optical scanning apparatus, the proximal end of the fiber is supported, whereas the distal end serving as a light output end is vibrated by being driven in two axial (x and y) directions that are orthogonal to the optical axis of the fiber and that are also orthogonal to each other. In this case, the phases in the two axial directions are shifted from each other by 90°, and the spiral scan is achieved by vibrating the distal end two-dimensionally in accordance with the same drive frequency while modulating and amplifying the amplitude of the vibration.

For example, PTL 1 discloses a technique in which a horizontal sine wave vibration drive signal and a vertical sine wave vibration drive signal whose phase is shifted by 90° from the horizontal signal are synchronized with each other and are amplitude-modulated in accordance with a triangular pattern so that a spiral scan pattern is formed.

PTL 2 discloses a technique for adjusting drive parameters, such as the amplitude of an applied voltage, the phase difference, and the drive frequency, while analyzing a spiral scan pattern acquired by an optical position detector (PSD) so that the scan pattern forms a perfect circle. In particular, the drive frequency is set close to the resonance frequency of the distal end of the fiber so that the maximum fiber amplitude can be obtained.

CITATION LIST

Patent literature

{PTL 1}
Japanese Patent No. 5190267
{PTL 2}
Japanese Unexamined Patent Application, Publication No. 2014-147462

SUMMARY OF INVENTION

An aspect of the present invention provides a drive-condition setting device applied to an optical scanning apparatus having a fiber and an actuator, the fiber optically guiding illumination light emitted from a light source and radiating the illumination light from its distal end onto an observation target, the actuator vibrating the distal end of the fiber with a predetermined drive frequency in two axial directions including an x direction and a y direction, the drive-condition setting device comprising: a scan-pattern detector that detects a scan pattern of the illumination light output from the distal end of the fiber; and a controller that measures resonance frequencies in the x direction and the y direction of the fiber and that sets drive conditions of the actuator based on the resonance frequencies and conduct control, wherein the controller sets a target amplitude of the scan pattern and sets a drive frequency and drive voltages such that the scan pattern detected by the scan-pattern detector is within a predetermined range with respect to the target amplitude and such that conditional expressions below are satisfied:
when fx>fy, $$fd<fy \text{ and } Vx \geq Vy \quad (1)$$

or $$fd>fx \text{ and } Vx \leq Vy \quad (2), \text{ and}$$

when fx≤fy, $$fd<fx \text{ and } Vx \leq Vy \quad (3)$$

or $$fd>fy \text{ and } Vx \geq Vy \quad (4)$$

where fd denotes the drive frequency, fx denotes the resonance frequency in the x direction, fy denotes the resonance frequency in the y direction, Vx denotes a maximum voltage with respect to a drive signal in the x direction, and Vy denotes a maximum voltage with respect to a drive signal in the y direction.

Another aspect of the present invention provides a drive-condition setting device applied to an optical scanning apparatus having a fiber and an actuator, the fiber optically guiding illumination light emitted from a light source and radiating the illumination light from its distal end onto an observation target, the actuator vibrating the distal end of the fiber with a predetermined drive frequency in two axial directions including an x direction and a y direction, the drive-condition setting device comprising: a controller that measures resonance frequencies in the x direction and the y direction of the fiber and that sets drive conditions based on the resonance frequencies and conducting control, wherein the controller calculates a difference in phase shift amounts between the x direction and the y direction based on a phase shift of a vibration waveform of the fiber with respect to the x direction and a phase shift of a vibration waveform of the fiber with respect to the y direction, and sets a corrected phase difference by correcting a phase difference in the y direction relative to the x direction such that conditional expressions below are satisfied:
when fx≤fy, $$\theta'=\theta-|\Delta\theta| \quad (5), \text{ and}$$

when fx>fy, $$\theta'=\theta+|\Delta\theta| \quad (6)$$

where fx denotes the resonance frequency in the x direction, fy denotes the resonance frequency in the y direction, θ' denotes the corrected phase difference, θ denotes the phase difference of a y-direction voltage waveform relative to that of the x direction, and $|\Delta\theta|$ denotes the difference in phase shift amounts between the x direction and the y direction.

Another aspect of the present invention provides a drive-condition setting method applied to an optical scanning apparatus having a fiber and an actuator, the fiber optically guiding illumination light emitted from a light source and radiating the illumination light from its distal end onto an observation target, the actuator vibrating the distal end of the fiber with a predetermined drive frequency in two axial directions including an x direction and a y direction, the drive-condition setting method comprising: a scan-pattern detecting step of detecting a scan pattern of the illumination light output from the distal end of the fiber; and a controlling step of measuring resonance frequencies in the x direction and the y direction of the fiber, setting drive conditions of the actuator based on the resonance frequencies, and conducting control, wherein the controlling step includes setting a target amplitude of the scan pattern and setting a drive frequency and drive voltages such that the scan pattern detected in the scan-pattern detecting step is within a predetermined range with respect to the target amplitude and such that conditional expressions below are satisfied:

when fx>fy, $$fd<fy \text{ and } Vx \geq Vy \quad (1)$$

or $$fd>fx \text{ and } Vx \leq Vy \quad (2), \text{ and}$$

when fx≤fy, $$fd<fx \text{ and } Vx \leq Vy \quad (3)$$

or $$fd>fy \text{ and } Vx \geq Vy \quad (4)$$

where fd denotes the drive frequency, fx denotes the resonance frequency in the x direction, fy denotes the resonance frequency in the y direction, Vx denotes a maximum voltage with respect to a drive signal in the x direction, and Vy denotes a maximum voltage with respect to a drive signal in the y direction.

Another aspect of the present invention provides a drive-condition setting method applied to an optical scanning apparatus having a fiber and an actuator, the fiber optically guiding illumination light emitted from a light source and radiating the illumination light from its distal end onto an observation target, the actuator vibrating the distal end of the fiber with a predetermined drive frequency in two axial directions including an x direction and a y direction, the drive-condition setting method comprising: a controlling step of measuring resonance frequencies in the x direction and the y direction of the fiber, setting drive conditions based on the resonance frequencies, and conducting control, wherein the controlling step includes calculating a difference in phase shift amounts between the x direction and the y direction based on a phase shift of a vibration waveform of the fiber with respect to the x direction and a phase shift of a vibration waveform of the fiber with respect to the y direction, and setting a corrected phase difference by correcting a phase difference in the y direction relative to the x direction such that conditional expressions below are satisfied:

when fx≤fy, $$\theta'=\theta-|\Delta\theta| \quad (5), \text{ and}$$

when fx>fy, $$\theta'=\theta+|\Delta\theta| \quad (6)$$

where fx denotes the resonance frequency in the x direction, fy denotes the resonance frequency in the y direction, $\theta'$ denotes the corrected phase difference, $\theta$ denotes the phase difference of a y-direction voltage waveform relative to that of the x direction, and $|\Delta\theta|$ denotes the difference in phase shift amounts between the x direction and the y direction.

DESCRIPTION OF EMBODIMENTS

First Embodiment

A drive-condition setting device according to a first embodiment of the present invention will be described below.

Figure 1:
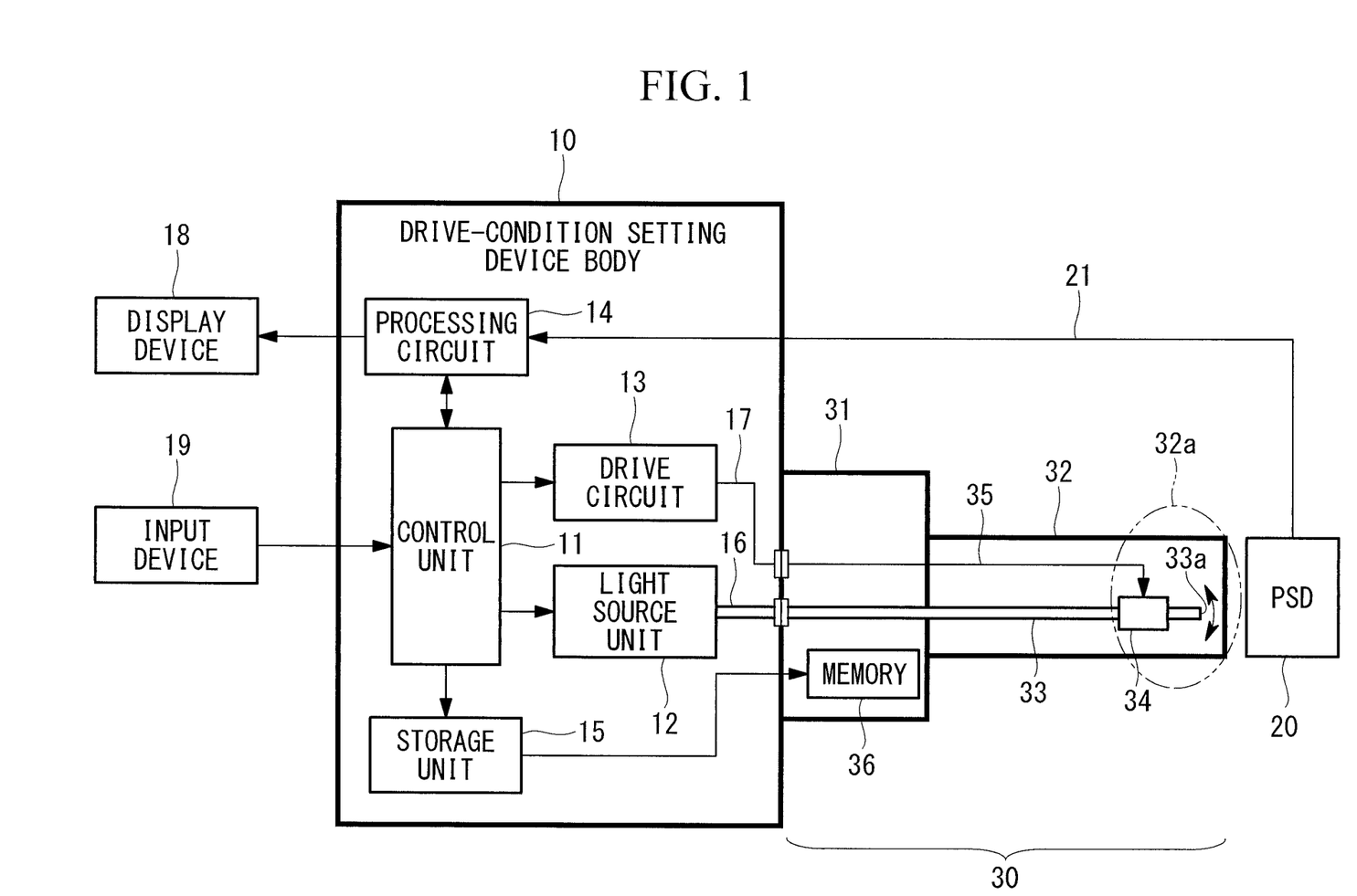
FIG. 1 is a block diagram illustrating a state where a drive-condition setting device according to a first embodiment of the present invention and an endoscope are connected to each other.

FIG. 1 illustrates a state where the drive-condition setting device according to this embodiment is connected to an insertion section 32 of an endoscope 30 serving as an optical scanning apparatus.

First, the endoscope 30 whose drive conditions are set by the drive-condition setting device according to this embodiment will be described.

The insertion section 32 of the endoscope 30 is provided with an illumination fiber 33 that optically guides illumination light, an actuator (driving mechanism) 34 that is provided at a distal end 33a of the illumination fiber 33 and that drives the distal end 33a, a drive signal line 35 that transmits a drive signal to the actuator 34, and a light-receiving fiber 37 (see FIG. 2) that receives reflection light or fluorescence produced as a result of the illumination light being radiated onto an observation target and that optically guides the reflection light or the fluorescence to the endoscope 30. The insertion section 32 is also provided with a memory 36 that stores the set drive conditions.

The insertion section 32 is connected to the body (not shown) of the endoscope 30 and is used for performing observation. The body of the endoscope 30 includes, for example, a light source that outputs illumination light to the illumination fiber, a drive circuit for driving the actuator 34, and an image processing circuit that processes the reflection light or the fluorescence optically guided by the light-receiving fiber to form an image.

The drive-condition setting device according to this embodiment is used for setting the drive conditions of the endoscope 30 before the product shipment. The endoscope 30 whose drive conditions are set generates an endoscopic image by being connected to the body of the endoscope 30, so that observation can be performed.

Figure 2:
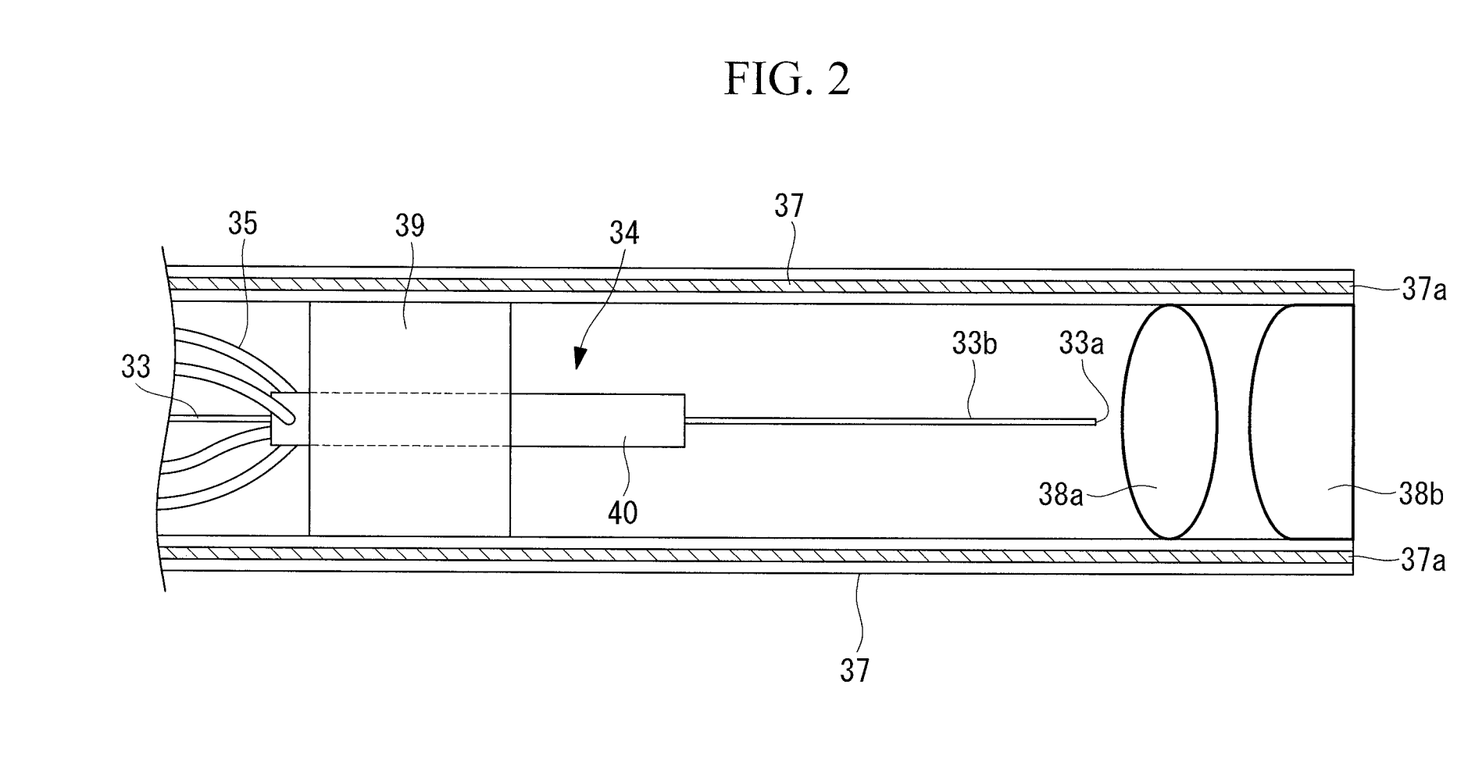
FIG. 2 is a cross-sectional view of a distal end of an insertion section of the endoscope in FIG. 1.
Figure 3:
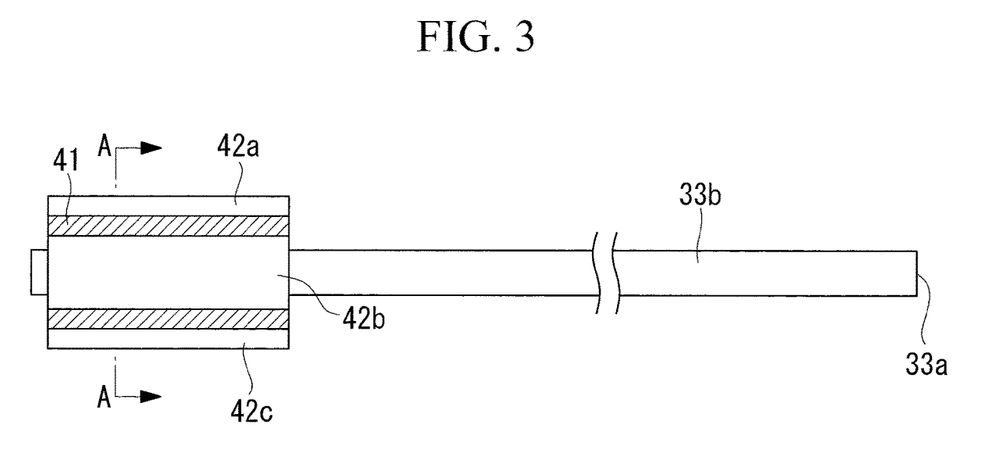
FIG. 3 is a side view illustrating an actuator of the endoscope together with an illumination fiber.
Figure 4:
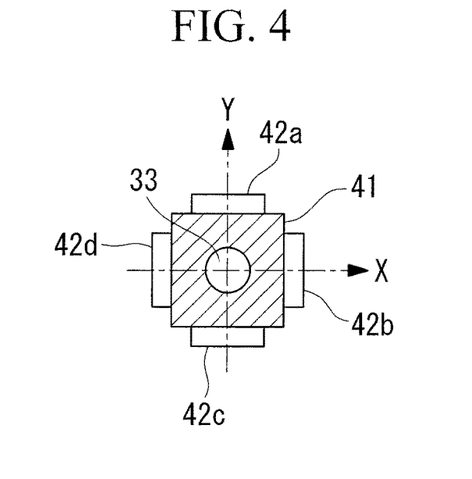
FIG. 4 is a cross-sectional view taken along line A-A in FIG. 3.

As shown in FIGS. 2 to 4, a distal end 32a (i.e., a part indicated by the dashed line in FIG. 1) of the insertion section 32 includes the illumination fiber 33 disposed at the center of the insertion section 32, the actuator 34 provided at the distal end of the illumination fiber 33, projection lenses 38a and 38b, and the light-receiving fiber 37 disposed at the outer periphery of the insertion section 32.

The actuator 34 includes an actuator tube 40 fixed inside the insertion section 32 by means of an attachment ring 39, and also includes a fiber support member 41 and piezoelectric elements 42a to 42d that are disposed within the actuator tube 40.

The illumination fiber 33 is supported by the fiber support member 41, and a segment of the illumination fiber 33 from the fiber support member 41 to the distal end 33a serves as an oscillating section 33b that is vibrated by the piezoelectric elements. The fiber support member 41 has four side surfaces that are orthogonal to each other and that are perpendicular to the light output direction (optical-axis direction) at the distal end 33a of the illumination fiber 33. Specifically, the four side surfaces of the fiber support member 41 are respectively oriented in the +x direction, +y direction, −x direction, and −y direction in FIG. 4 such that adjacent side surfaces of the four side surfaces are orthogonal to each other.

The pair of piezoelectric elements 42a and 42c for driving in the y direction are fixed to the +y side and the −y side of the fiber support member 41, and the pair of piezoelectric elements 42b and 42d for driving in the x direction are fixed to the +x side and the −x side. In each pair of piezoelectric elements disposed to face each other with the fiber support member 41 interposed therebetween, one of the piezoelectric elements contracts when the other expands, thus causing the fiber support member 41 to deform. Each pair of piezoelectric elements alternately repeat this process so as to cause vibration to occur in the x and y directions.

The illumination light output from the illumination fiber 33 vibrated in this manner is focused on the observation target by the projection lenses 38a and 38b. Therefore, a PSD 20 is disposed such that a light-receiving surface thereof is aligned with the focal position.

The drive-condition setting device will be described, while referring back to FIG. 1.

The drive-condition setting device includes a drive-condition setting device body 10 and a scan-pattern detector (PSD) 20. The drive-condition setting device body 10 may be appropriately connected to a display device 18, such as a display, and an input device 19, such as a keyboard or a mouse.

The drive-condition setting device body 10 includes a controller 11 that totally controls the drive-condition setting device body 10, a light source unit 12 that supplies the endoscope 30 with illumination light for setting the drive conditions, a drive circuit 13 that drives the actuator 34 of the endoscope 30, an processing circuit 14 that performs a predetermined process in accordance with an output from the PSD 20, and a storage unit 15 that stores drive parameters indicating the drive conditions output from the processing circuit 14.

The light source unit 12 includes a light source, such as a laser diode or a diode pumped solid state (DPSS) laser, and outputs illumination light for setting the drive conditions in accordance with a control signal from the controller 11. The light source unit 12 is connected to an illumination fiber 16, and the illumination fiber 16 is coupled to the illumination fiber 33 of the endoscope 30 via a connection section 31. The illumination light emitted from the light source is output to the illumination fiber 16 and is then output to the illumination fiber 33 via the connection section 31.

The drive circuit 13 supplies a drive signal to the actuator 34 of the endoscope 30. The drive signal is supplied to the actuator 34 via a drive signal line 17 connected to the drive circuit 13, the connection section 31, and a drive signal line 35.

In this embodiment, the actuator 34 is configured to drive the illumination fiber 33 by using the piezoelectric elements. Therefore, in this case, the drive circuit 13 supplies drive voltages to the piezoelectric elements.

More specifically, in accordance with a command from the controller 11, the drive circuit 13 applies drive voltages with a predetermined frequency to the piezoelectric elements 42b and 42d for driving in the x direction and the piezoelectric elements 42a and 42c for driving in the y direction, so as to cause the illumination fiber 33 to vibrate. When the piezoelectric elements 42b and 42d for driving in the x direction and the piezoelectric elements 42a and 42c for driving in the y direction are driven, the oscillating section 33b at the distal end of the illumination fiber 33 vibrates, causing the distal end 33a to deflect periodically. Consequently, the illumination light output from the distal end 33a is scanned over the light-receiving surface of the PSD 20.

Figure 5:
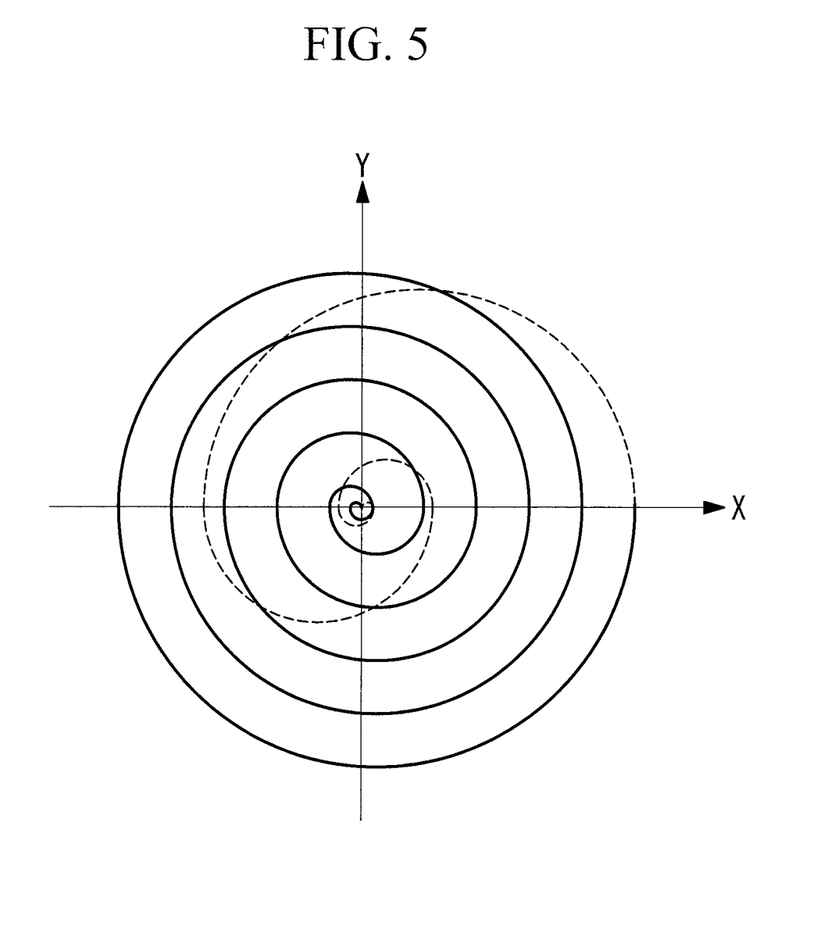
FIG. 5 is a reference diagram illustrating an example of a scan pattern of a spiral scan.

In particular, by applying drive voltages that have the same drive frequency in the x and y directions and have phases different from each other by 90° and whose amplitude changes between 0 and the maximum value, the light is scanned to form a spiral scan pattern on the light-receiving surface of the PSD 20 (see FIG. 5). In FIG. 5, a solid line shows an example of a scan pattern obtained when the amplitude is increased, and a dashed line shows a scan pattern obtained when the amplitude is reduced.

Figure 6:
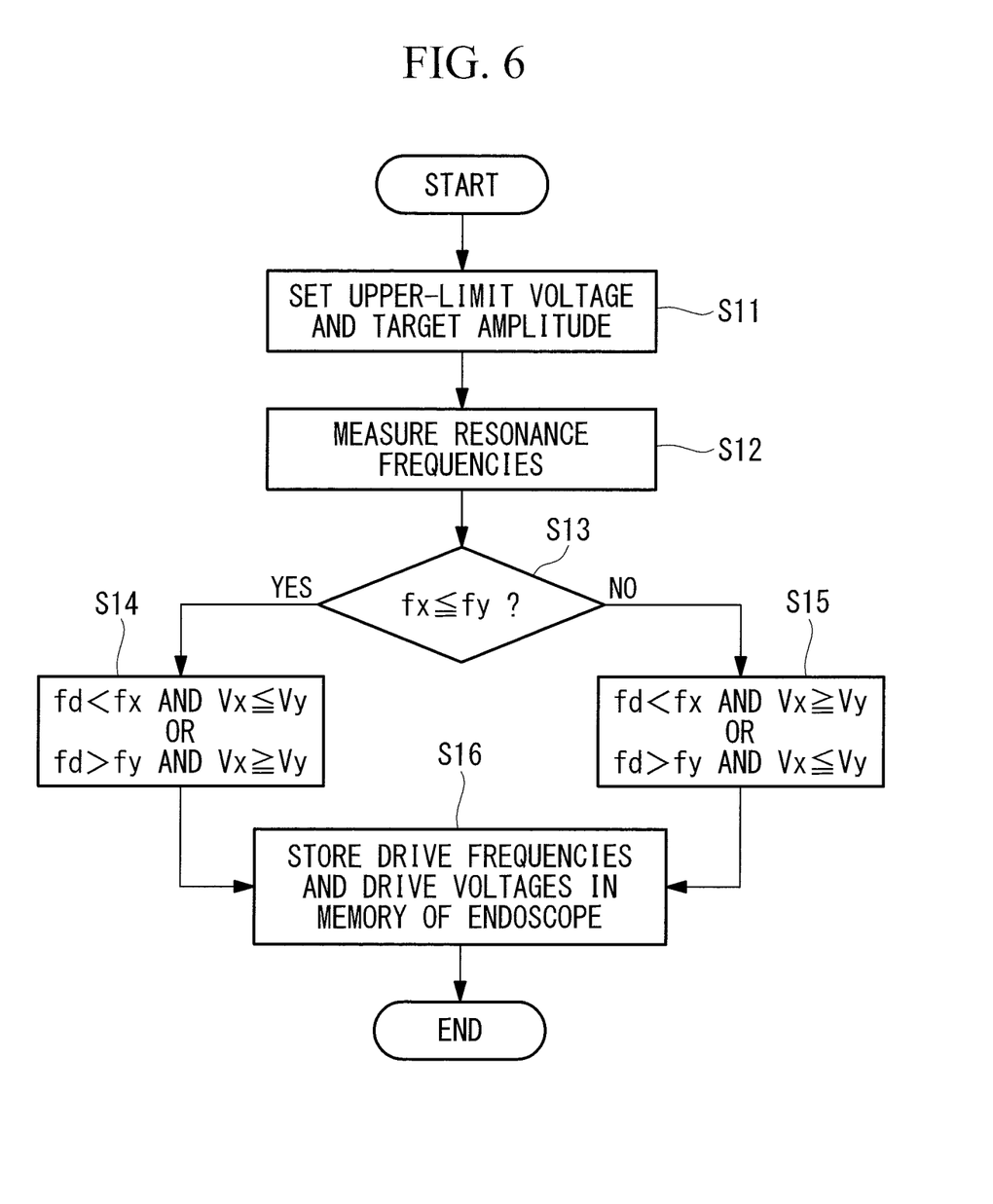
FIG. 6 is a flowchart of a method used by the drive-condition setting device in FIG. 1 for setting drive conditions of the endoscope.

Next, a method of setting the drive conditions of the endoscope by using the drive-condition setting device having the above-described configuration will be described with reference to a flowchart in FIG. 6.

When setting the drive conditions, the drive-condition setting device is connected to the insertion section 32 of the endoscope 30 as a setting target. Specifically, as shown in FIG. 1, the drive-condition setting device body 10 and the insertion section 32 are connected to each other by means of the connection section 31, thereby coupling the illumination fiber 16 and the illumination fiber 33 to each other and also connecting the drive signal line 17 and the drive signal line 35 to each other. Moreover, the PSD is disposed such that the illumination light output from the insertion section 32 is focused onto the light-receiving surface of the PSD and such that the origin of coordinates of the PSD 20 is positioned on the optical axis in a state where the illumination fiber 33 does not vibrate.

When the drive-condition setting device and the endoscope 30 are connected to each other, an upper-limit voltage to be applied to the piezoelectric elements 42a to 42d and a target amplitude are set in step S11. With regard to each piezoelectric element, the interior of the crystal thereof is polarized when a voltage is applied thereto, causing deformation to occur. However, when an excessive voltage is applied, the piezoelectric element may possibly become damaged. Therefore, the piezoelectric elements 42a to 42d are prevented from being damaged by setting an upper-limit voltage in advance. Furthermore, since the drive conditions of the piezoelectric elements 42a to 42d are also dependent on the scan range of the illumination light, a target amplitude is set as a desired irradiation range of the illumination light.

Subsequently, in step S12, resonance frequencies fx and fy in the x and y directions are measured. Specifically, for each of the x and y directions, a drive voltage is applied to the actuator 34 from the drive circuit while changing the frequency, and the amplitude of illumination light output from the distal end 33a of the illumination fiber 33 is detected by the PSD 20, so that the frequency at which the maximum amplitude is obtained can be set as a resonance frequency. Alternatively, the drive-condition setting device body 10 may be provided with, for example, an impedance analyzer, and the resonance frequency may be measured in accordance with an impedance measuring process while changing the drive frequency of the illumination fiber 33.

Subsequently, in step S13, the resonance frequencies fx and fy previously measured in step S12 are compared, and the drive conditions are set in accordance with the comparison result such that the following conditional expressions are satisfied:

when fx>fy, $$fd<fy \text{ and } Vx \geq Vy \quad (1)$$

or $$fd>fx \text{ and } Vx \leq Vy \quad (2), \text{ and}$$

when fx≤fy, $$fd<fx \text{ and } Vx \leq Vy \quad (3)$$

or $$fd>fy \text{ and } Vx \geq Vy \quad (4)$$

where fd denotes a drive frequency, fx denotes a resonance frequency in the x direction, fy denotes a resonance frequency in the y direction, Vx denotes a voltage with respect to a drive signal in the x direction, and Vy denotes a voltage with respect to a drive signal in the y direction.

Although there are various conceivable procedures for setting the drive conditions that satisfy any one of the above conditional expressions (1) to (4), for example, the drive conditions may be set as follows.

Figure 7:
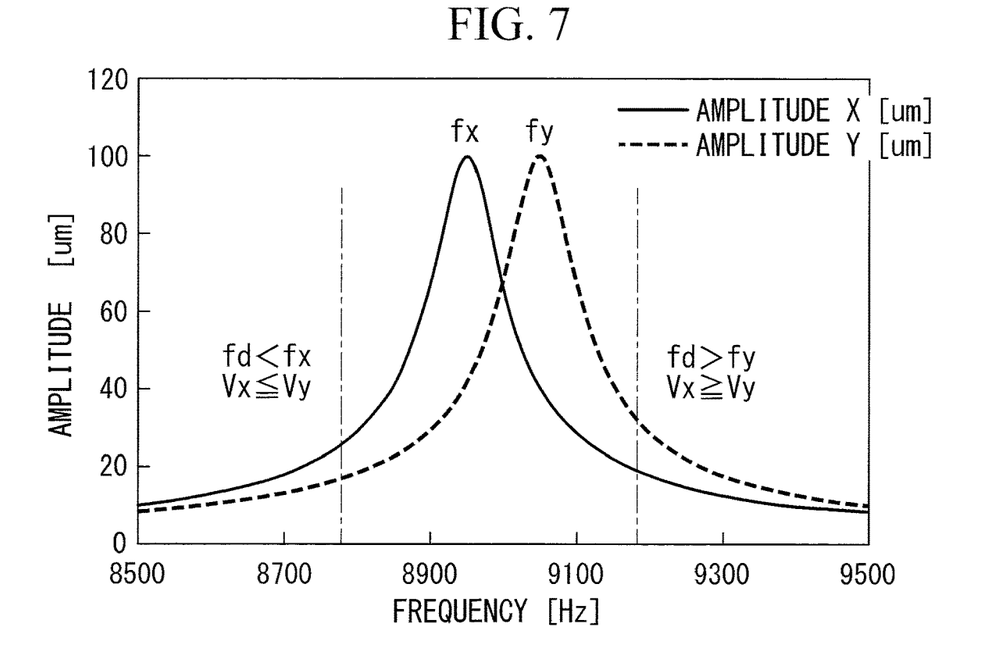
FIG. 7 illustrates an example of frequency characteristics of the x-direction amplitude and the y-direction amplitude of a distal end of the illumination fiber, and is specifically a graph illustrating an example when fx≤fy.

When fx≤fy and drive conditions that satisfy fd<fx and Vx≤Vy of the conditional expression (3) are to be set, the drive conditions are set as follows (see FIG. 7).

Specifically, because fx≤fy is satisfied as a result of the determination in step S13, the process proceeds to step S14. In step S14, a drive voltage Vymax for the y direction is set, and an initial value fd0 of the drive frequency fd is arbitrarily set within a range fd<fx.

Then, the distal end 33a of the illumination fiber 33 is vibrated in the y direction by the actuator 34 while light is emitted from the light source unit 12. By using the controller 11 to control the drive circuit 13, the drive frequency applied for scanning in the y direction is gradually increased. In this case, the irradiation position of the illumination light is detected by the PSD 20, the detected irradiation position is output to the processing circuit 14 via a detection signal line 21, and a scan pattern in the y direction is calculated by the processing circuit 14. As the drive frequency gradually increases, the scan amplitude gradually increases to approach the target amplitude. The controller 11 compares the target amplitude with the scan amplitude, sets the drive frequency fd when the scan amplitude substantially matches the target amplitude, and ends the scan in the y direction.

As mentioned above, since the drive voltage Vy is already set, the drive voltage Vx is subsequently set. The drive circuit 13 causes the actuator 34 to perform a scan in the x direction with the previously-set drive frequency fd while the controller 11 causes the light source unit 12 to emit light, and the PSD 20 detects the irradiation position of the illumination light. In this case, the drive voltage Vx is gradually increased from 0 so that the scan amplitude in the x direction is increased and a voltage at which the scan amplitude becomes close to the target amplitude is set as the drive voltage Vx, and the scan ends.

In other words, when the driving is performed with the previously-set drive frequency fd, the drive voltage Vx corresponding to the target amplitude exists in the range 0<Vx<Vy (Vmax) so that Vx becomes lower than Vy. Therefore, when setting the drive conditions, a drive frequency and a drive voltage by which the voltage value becomes higher either in the x direction or the y direction are first set from the above conditional expressions, and a drive voltage by which the voltage value becomes low is subsequently set.

When fx≤fy and drive conditions that satisfy fd>fx and Vx≥Vy of the conditional expression (4) are to be set, the drive conditions are set as follows (see FIG. 7).

Specifically, because fx≤fy is satisfied as a result of the determination in step S13, the process proceeds to step S14. In step S14, a drive frequency is set by performing a one-dimensional scan in the x direction. Specifically, a drive voltage Vxmax for the x direction is first set, and an initial value fd0 of the drive frequency fd is arbitrarily set within a range fd>fx.

Then, the distal end 33a of the illumination fiber 33 is vibrated in the x direction by the actuator 34 while light is emitted from the light source unit 12. By using the controller 11 to control the drive circuit 13, the drive frequency applied for scanning in the x direction is gradually decreased. In this case, the irradiation position of the illumination light is detected by the PSD 20, and a scan pattern in the x direction is calculated by the processing circuit 14 via the detection signal line 21. As the drive frequency gradually decreases, the scan amplitude gradually increases to approach the target amplitude. The controller 11 compares the target amplitude with the scan amplitude, sets the drive frequency fd when the scan amplitude substantially matches the target amplitude, and ends the scan in the x direction.

As mentioned above, since the drive voltage Vx is already set, the drive voltage Vy is subsequently set. The drive circuit 13 causes the actuator 34 to perform a scan in the y direction with the previously-set drive frequency fd while the controller 11 causes the light source unit 12 to emit light, and the PSD 20 detects the irradiation position of the illumination light. In this case, the drive voltage Vy is gradually increased from 0 so that the scan amplitude in the x direction is increased and a voltage at which the scan amplitude becomes close to the target amplitude is set as the drive voltage Vy, and the scan ends.

In other words, when the driving is performed with the previously-set drive frequency fd, the drive voltage Vy corresponding to the target amplitude exists in the range 0<Vy<Vx (Vmax) so that Vy becomes lower than Vx. Therefore, when setting the drive conditions, a drive frequency and a drive voltage by which the voltage value becomes higher either in the x direction or the y direction are first set from the above conditional expressions, and a drive voltage by which the voltage value becomes low is subsequently set.

When fx≤fy, the drive conditions may be set such that either one of the above conditional expressions (3) or (4) is satisfied.

Figure 8:
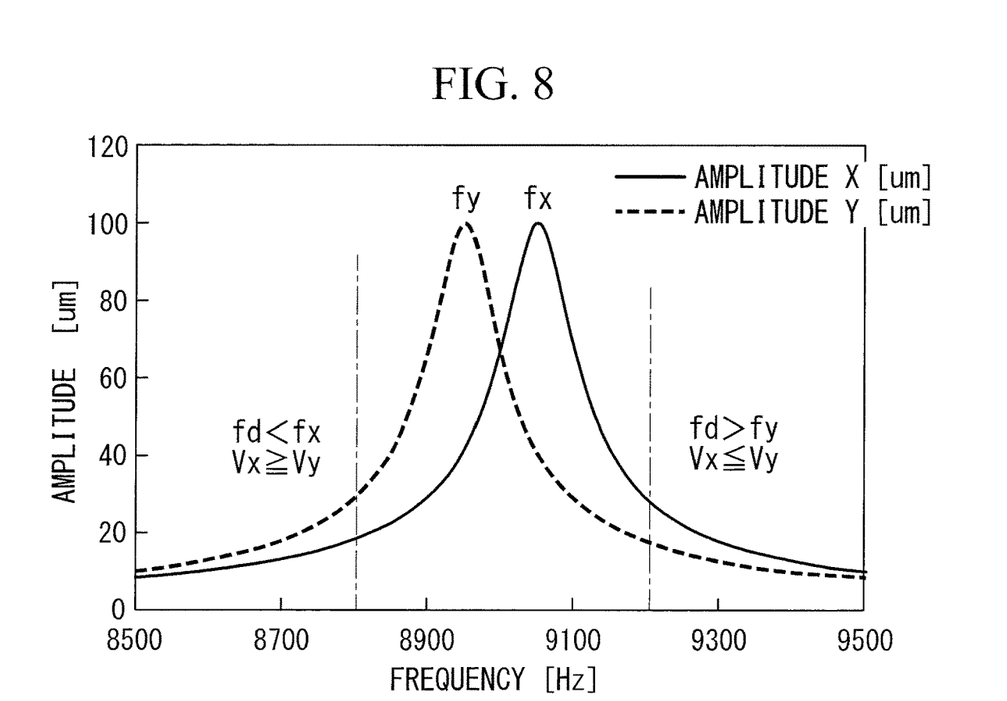
FIG. 8 illustrates an example of frequency characteristics of the x-direction amplitude and the y-direction amplitude of the distal end of the illumination fiber, and is specifically a graph illustrating an example when fx>fy.

When fx>fy and drive conditions that satisfy fd<fy and Vx≥Vy of the conditional expression (1) are to be set, the drive conditions are set as follows (see FIG. 8).

Specifically, because fx≤fy is not satisfied as a result of the determination in step S13, the process proceeds to step S15. In step S15, a drive voltage Vxmax for the x direction is set and an initial value fd0 of the drive frequency fd is arbitrarily set within a range fd<fy.

Then, the distal end 33a of the illumination fiber 33 is vibrated in the x direction by the actuator 34 while light is emitted from the light source unit 12. By using the controller 11 to control the drive circuit 13, the drive frequency applied for scanning in the x direction is gradually increased. In this case, the irradiation position of the illumination light is detected by the PSD 20, and a scan pattern in the x direction is calculated by the processing circuit 14 via the detection signal line 21. As the drive frequency gradually increases, the scan amplitude gradually increases to approach the target amplitude. The controller 11 compares the target amplitude with the scan amplitude, sets the drive frequency fd when the scan amplitude substantially matches the target amplitude, and ends the scan in the x direction.

As mentioned above, since the drive voltage Vx is already set, the drive voltage Vy is subsequently set. The drive circuit 13 causes the actuator 34 to perform a scan in the y direction with the previously-set drive frequency fd while the controller 11 causes the light source unit 12 to emit light, and the PSD 20 detects the irradiation position of the illumination light. In this case, the drive voltage Vy is gradually increased from 0 so that the scan amplitude in the x direction is increased and a voltage at which the scan amplitude becomes close to the target amplitude is set as the drive voltage Vy, and the scan ends.

In other words, when the driving is performed with the previously-set drive frequency fd, the drive voltage Vy corresponding to the target amplitude exists in the range 0<Vy<Vx (Vmax) so that Vy becomes lower than Vx. Therefore, when setting the drive conditions, a drive frequency and a drive voltage by which the voltage value becomes higher either in the x direction or the y direction are first set from the above conditional expressions, and a drive voltage by which the voltage value becomes low is subsequently set.

When fx>fy and drive conditions that satisfy fd>fx and Vx≤Vy of the conditional expression (2) are to be set, the drive conditions are set as follows (see FIG. 8).

Specifically, because fx≤fy is not satisfied as a result of determination in step S13, the process proceeds to step S15.

In step S15, a drive frequency is set by performing a one-dimensional scan in the y direction. Specifically, a drive voltage Vymax for the y direction is first set, and an initial value fd0 of the drive frequency fd is arbitrarily set within a range fd>fx.

Then, the distal end 33a of the illumination fiber 33 is vibrated in the y direction by the actuator 34 while light is emitted from the light source unit 12. By using the controller 11 to control the drive circuit 13, the drive frequency applied for scanning in the y direction is gradually decreased. In this case, the irradiation position of the illumination light is detected by the PSD 20, and a scan pattern in the y direction is calculated by the processing circuit 14 via the detection signal line 21. As the drive frequency gradually decreases, the scan amplitude gradually increases to approach the target amplitude. The controller 11 compares the target amplitude with the scan amplitude, sets the drive frequency fd when the scan amplitude substantially matches the target amplitude, and ends the scan in the y direction.

As mentioned above, since the drive voltage Vy is already set, the drive voltage Vx is subsequently set. The drive circuit 13 causes the actuator 34 to perform a scan in the x direction with the previously-set drive frequency fd while the controller 11 causes the light source unit 12 to emit light, and the PSD 20 detects the irradiation position of the illumination light. In this case, the drive voltage Vx is gradually increased from 0 so that the scan amplitude in the x direction is increased and a voltage at which the scan amplitude becomes close to the target amplitude is set as the drive voltage Vx, and the scan ends.

In other words, when the driving is performed with the previously-set drive frequency fd, the drive voltage Vx corresponding to the target amplitude exists in the range 0<Vx<Vy (Vmax) so that Vx becomes lower than Vy. Therefore, when setting the drive conditions, a drive frequency and a drive voltage by which the voltage value becomes higher either in the x direction or the y direction are first set from the above conditional expressions, and a drive voltage by which the voltage value becomes low is subsequently set.

When fx>fy, the drive conditions may be set such that either one of the above conditional expressions (1) or (2) is satisfied.

In step S16, the drive conditions set in this manner, such as the drive frequencies and the drive voltages for the x and y directions, are stored in the memory of the endoscope 30, so that the process for setting the drive conditions ends.

Accordingly, resonance frequencies in the x and y directions are measured, and based on the magnitude relationship therebetween, optimal drive frequencies and drive voltages are set. Therefore, even if an optical scanning apparatus whose drive conditions are to be set has an asymmetrical shape such that the resonance frequencies in the x and y directions are different from each other, drive conditions with which an optimal visual-field range can be obtained without distortion can be appropriately set. As an alternative to the above example in which the controller 11 compares the target amplitude with the scan amplitude and sets the drive frequency when the scan amplitude substantially matches the target amplitude, the drive frequency may be set such that the scan amplitude is within a predetermined range of the target amplitude.

Second Embodiment

A drive-condition setting device according to a second embodiment of the present invention will be described below.

The drive-condition setting device according to this embodiment has a configuration identical to that in the first embodiment described above. Therefore, the description of the configuration will be omitted, and an endoscope drive-condition setting method performed by the drive-condition setting device according to this embodiment will be described with reference to a flowchart in FIG. 9.

When setting the drive conditions, the drive-condition setting device is connected to the insertion section 32 of the endoscope 30 serving as a setting target. Specifically, as shown in FIG. 1, the drive-condition setting device body 10 and the insertion section 32 are connected to each other by means of the connection section 31, thereby coupling the illumination fiber 16 and the illumination fiber 33 to each other and also connecting the drive signal line 17 and the drive signal line 35 to each other. Moreover, the PSD is disposed such that the illumination light output from the insertion section 32 is focused onto the light-receiving surface of the PSD and such that the origin of coordinates of the PSD 20 is positioned on the optical axis in a state where the illumination fiber 33 does not vibrate.

Figure 9:
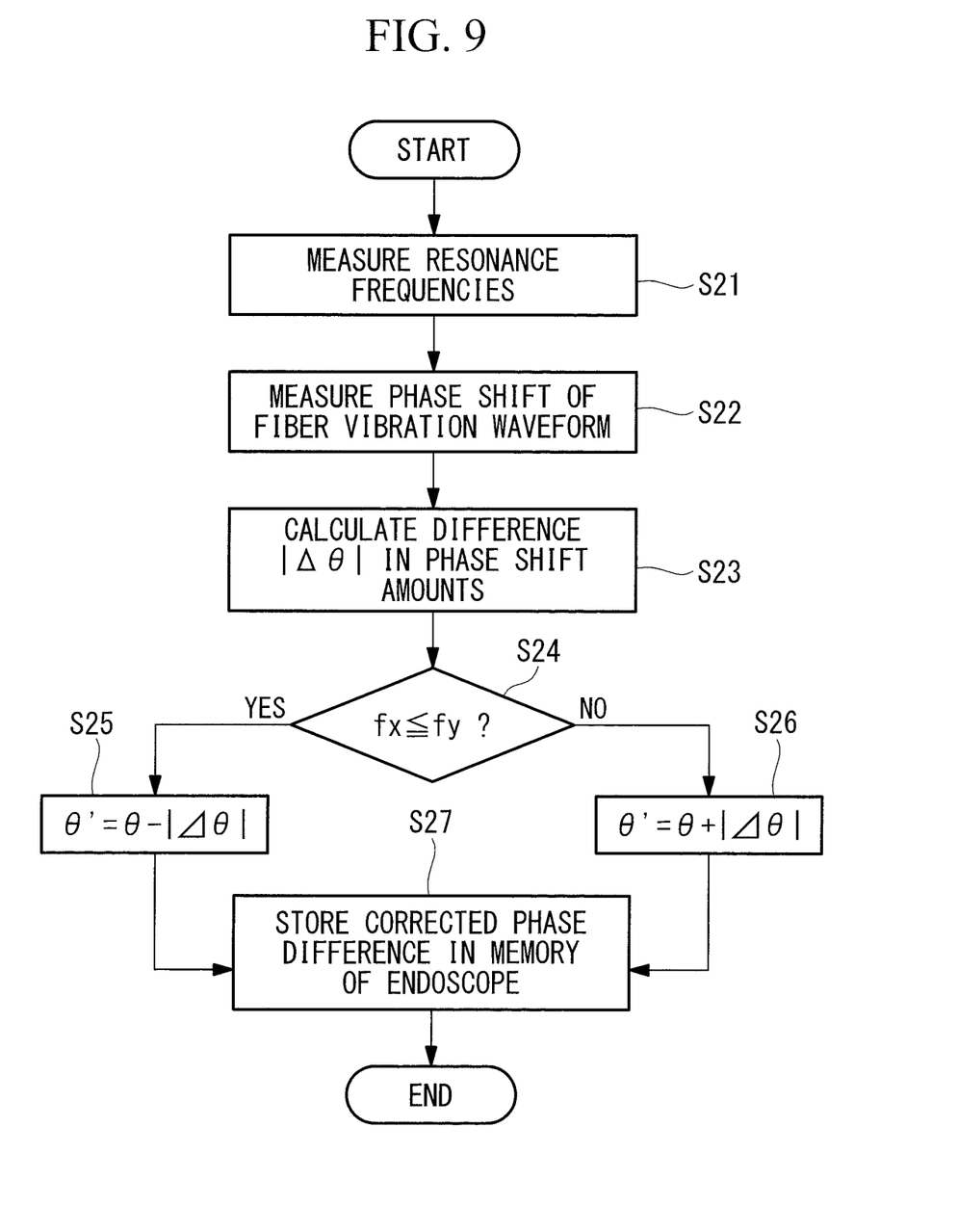
FIG. 9 is a flowchart of a method used by a drive-condition setting device according to a second embodiment of the present invention for setting drive conditions of an endoscope.

When the drive-condition setting device and the endoscope 30 are connected to each other, the resonance frequencies fx and fy in the x and y directions are measured in step S21. Specifically, for each of the x and y directions, a drive voltage is applied to the actuator 34 from the drive circuit while changing the frequency, and the amplitude of illumination light output from the distal end 33a of the illumination fiber 33 is detected by the PSD 20, so that the frequency at which the maximum amplitude is obtained can be set as a resonance frequency. Alternatively, the drive-condition setting device body 10 may be provided with, for example, an impedance analyzer, and the resonance frequency may be measured in accordance with an impedance measuring process while changing the drive frequency of the illumination fiber 33.

Figure 10:
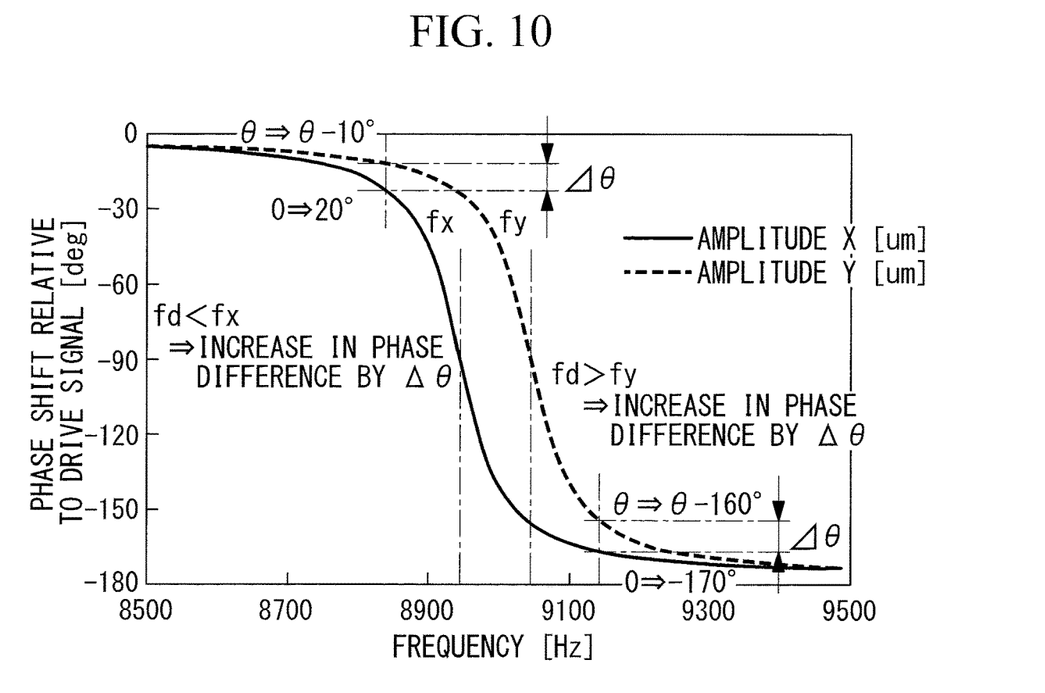
FIG. 10 illustrates a relationship between a phase shift and a frequency relative to x-direction and y-direction drive signals at the distal end of the illumination fiber, and is specifically a graph illustrating an example when fx≤fy.
Figure 11:
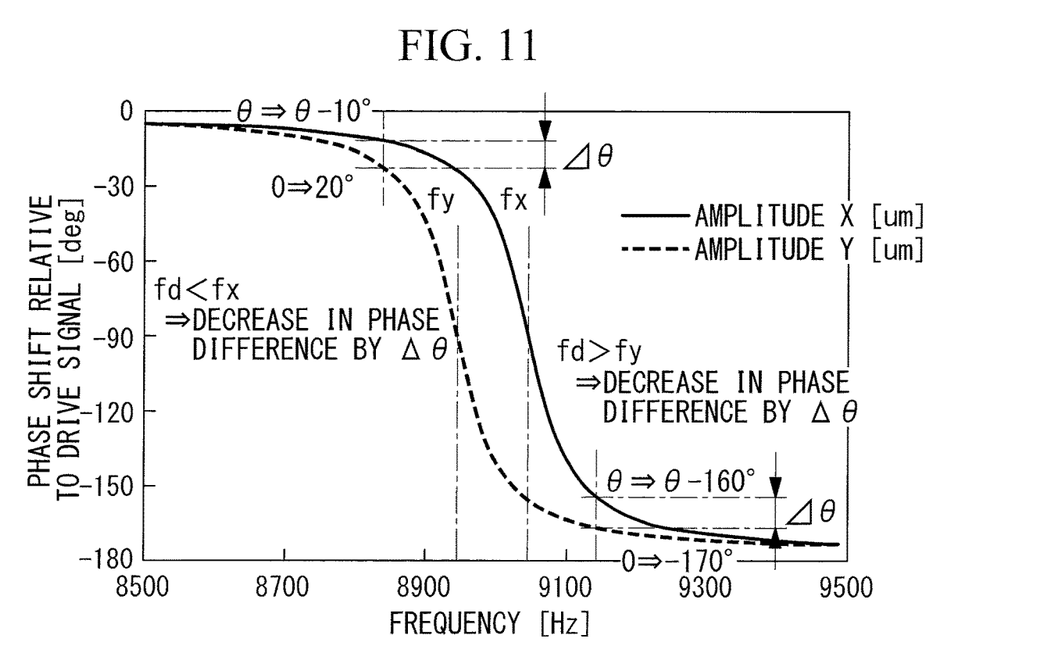
FIG. 11 illustrates a relationship between a phase shift and a frequency relative to x-direction and y-direction drive signals at the distal end of the illumination fiber, and is specifically a graph illustrating an example when fx>fy.

Subsequently, in step S22, a phase shift of a fiber vibration waveform of the distal end of the illumination fiber 33 relative to a drive voltage waveform at the drive frequency, that is, a time response, is measured for each of the x and y directions (see FIGS. 10 and 11).

Although there are various conceivable methods for measuring the phase shift, a method that uses the PSD 20 will be described in this embodiment.

In step S22, a drive signal is input to the actuator 34 from the drive circuit 13 for each of the x and y directions, and the vibration amplitude at the distal end of the illumination fiber 33 vibrated in accordance with the drive signal is measured by the PSD 20. The timing at which the PSD 20 performs the measurement and the timing at which the drive voltage is applied by the drive circuit 13 is synchronized so that the time response of the fiber vibration waveform at the distal end of the illumination fiber 33 relative to the drive voltage waveform is determined, and the time response is converted into a phase. By determining the phase for each drive frequency, graphs shown in FIGS. 10 and 11 can be obtained.

Subsequently, in step S23, a difference $|\Delta\theta|$ between the x-direction phase shift and the y-direction phase shift is calculated based on the x-direction phase shift and the y-direction phase shift determined in step S22. The process then proceeds to step S24.

The resonance frequencies fx and fy previously measured in step S21 are compared, and the drive conditions are set in accordance with the comparison result such that the following conditional expressions are satisfied. Specifically, based on the comparison result of the resonance frequencies fx and fy, a phase difference $\theta$ of a y-direction voltage waveform relative to the x direction is corrected as follows, so that a corrected phase difference $\theta'$ is calculated.

If fx≤fy, the process proceeds to step S25. In step S25, the corrected phase difference $\theta'$ is calculated in accordance with the following conditional expression (5):

$$\theta' = \theta - |\Delta\theta| \tag{5}$$

If fx>fy, the process proceeds to step S26. In step S26, the corrected phase difference $\theta'$ is calculated in accordance with the following conditional expression (6):

$$\theta' = \theta + |\Delta\theta| \tag{6}$$

In this case, $\theta$ denotes the phase difference of the y-direction voltage waveform relative to the x direction, and $\theta'$ denotes the corrected phase difference.

Specifically, if it is desired that the scan pattern form a circle, the phase difference $\theta$ may be set close to 90 degrees. If the scan angles in the x and y directions are not orthogonal to each other, the phase difference $\theta$ is slightly deviated from 90 degrees in view of the deviation. The corrected phase difference is calculated from this state. As shown in FIG. 10, when fx≤fy and the driving is to be performed with the drive frequency indicated by a dashed line, since it can be read that $|\Delta\theta|=10°$ from the graph, the corrected phase difference $\theta'$ is set close to $\theta-10°$. Therefore, for example, a function of an x-direction drive waveform and a function of a y-direction drive waveform may be as follows:

x direction: $Vx(t) \times \sin(2\pi \times fd \times t)$ y direction: $Vy(t) \times \sin(2\pi \times fd \times t + \theta - 10°)$ In this case, Vx(t) and Vy(t) are functions related to x-direction and y-direction modulation sections of a voltage waveform.

In step S27, the corrected phase difference $\theta'$ set in this manner is stored in the memory of the endoscope 30, and the process for setting the drive conditions ends.

Accordingly, a phase shift from a vibration waveform of the distal end of the fiber is measured for each of the x and y directions so that even if an optical scanning apparatus is asymmetrical and the resonance frequencies in the x and y directions are different from each other, the difference can be readily ascertained. Based on the magnitude relationship between the resonance frequencies in the x and y directions, a corrected phase difference $\theta'$ is calculated by correcting the phase difference using a difference $|\Delta\theta|$ in phase shift amounts, indicating the difference between the phase shift in the x direction and the phase shift in the y direction, so that drive conditions with which an optimal visual-field range can be obtained without distortion can be appropriately set separately from the resonance frequencies.

The drive-condition setting method according to this embodiment for setting a corrected phase difference may be performed in addition to the process for setting the drive frequency and the drive voltage in accordance with the first embodiment described above.

Furthermore, as an alternative to the above-described example applied to an endoscope as an example of an optical scanning apparatus, the above-described example may be applied to, for example, an optical scanning microscope or an optical scanning projection apparatus, and may be used for setting the drive conditions thereof.

The inventors of the present invention have arrived at the following aspects of the present invention.

An aspect of the present invention provides a drive-condition setting device applied to an optical scanning apparatus having a fiber and an actuator, the fiber optically guiding illumination light emitted from a light source and radiating the illumination light from its distal end onto an observation target, the actuator vibrating the distal end of the fiber with a predetermined drive frequency in two axial directions including an x direction and a y direction, the drive-condition setting device comprising: a scan-pattern detector that detects a scan pattern of the illumination light output from the distal end of the fiber; and a controller that measures resonance frequencies in the x direction and the y direction of the fiber and that sets drive conditions of the actuator based on the resonance frequencies and conduct control, wherein the controller sets a target amplitude of the scan pattern and sets a drive frequency and drive voltages such that the scan pattern detected by the scan-pattern detector is within a predetermined range with respect to the target amplitude and such that conditional expressions below are satisfied:

when fx>fy, $$fd<fy \text{ and } Vx \geq Vy \quad (1)$$

or $$fd>fx \text{ and } Vx \leq Vy \quad (2), \text{ and}$$

when fx≤fy, $$fd<fx \text{ and } Vx \leq Vy \quad (3)$$

or $$fd>fy \text{ and } Vx \geq Vy \quad (4)$$

where fd denotes the drive frequency, fx denotes the resonance frequency in the x direction, fy denotes the resonance frequency in the y direction, Vx denotes a maximum voltage with respect to a drive signal in the x direction, and Vy denotes a maximum voltage with respect to a drive signal in the y direction.

According to the above aspect, when the device is applied to an optical scanning apparatus and is used for setting the drive conditions of the optical scanning apparatus, the controller measures the resonance frequencies in the x and y directions of the fiber of the optical scanning apparatus, compares the x-direction resonance frequency with the y-direction resonance frequency, and sets the drive conditions while comparing the scan pattern detected by the scan-pattern detector with the target amplitude. In this case, the drive conditions are set such that the scan pattern detected by the scan-pattern detector is within the predetermined range with respect to the target amplitude and such that any one of the conditional expressions (1) to (4) is satisfied. Consequently, drive conditions with which an optimal visual-field range can be obtained while distortion can be appropriately set even when the resonance frequencies in the x and y directions are different from each other.

In the above aspect, when the controller sets the drive frequency and the drive voltage, it is preferable that the controller firstly sets the drive frequency and the drive voltage for a direction in which a voltage value becomes relatively higher between the drive voltage for the x direction and the drive voltage for the y direction, satisfying the conditional expressions (1) to (4), and subsequently sets the drive voltage for a direction in which the voltage value becomes low.

Accordingly, optimal drive conditions can be readily set.

Another aspect of the present invention provides a drive-condition setting device applied to an optical scanning apparatus having a fiber and an actuator, the fiber optically guiding illumination light emitted from a light source and radiating the illumination light from its distal end onto an observation target, the actuator vibrating the distal end of the fiber with a predetermined drive frequency in two axial directions including an x direction and a y direction, the drive-condition setting device comprising: a controller that measures resonance frequencies in the x direction and the y direction of the fiber and that sets drive conditions based on the resonance frequencies and conducting control, wherein the controller calculates a difference in phase shift amounts between the x direction and the y direction based on a phase shift of a vibration waveform of the fiber with respect to the x direction and a phase shift of a vibration waveform of the fiber with respect to the y direction, and sets a corrected phase difference by correcting a phase difference in the y direction relative to the x direction such that conditional expressions below are satisfied:

when fx≤fy, $$\theta' = \theta - |\Delta\theta| \quad (5), \text{ and}$$

when fx>fy, $$\theta' = \theta + |\Delta\theta| \quad (6)$$

where fx denotes the resonance frequency in the x direction, fy denotes the resonance frequency in the y direction, θ' denotes the corrected phase difference, θ denotes the phase difference of a y-direction voltage waveform relative to that of the x direction, and |Δθ| denotes the difference in phase shift amounts between the x direction and the y direction.

According to the above aspect, the device is applied to an optical scanning apparatus, measures the resonance frequencies in the x and y directions of the fiber of the optical scanning apparatus, and measures a phase shift from the vibration waveform of the distal end of the fiber for each of the x and y directions. Therefore, even when the optical scanning apparatus is asymmetrical and the resonance frequencies in the x and y directions are different from each other, the difference can be readily ascertained. Based on the magnitude relationship between the resonance frequencies in the x and y directions, a corrected phase difference θ' is calculated by correcting the phase difference using a difference in phase shift amounts, indicating the difference between the phase shift in the x direction and the phase shift in the y direction, so that drive conditions with which an optimal visual-field range can be obtained while distortion can be appropriately set separately from the resonance frequencies.

Another aspect of the present invention provides a drive-condition setting method applied to an optical scanning apparatus having a fiber and an actuator, the fiber optically guiding illumination light emitted from a light source and radiating the illumination light from its distal end onto an observation target, the actuator vibrating the distal end of the fiber with a predetermined drive frequency in two axial directions including an x direction and a y direction, the drive-condition setting method comprising: a scan-pattern detecting step of detecting a scan pattern of the illumination light output from the distal end of the fiber; and a controlling step of measuring resonance frequencies in the x direction and the y direction of the fiber, setting drive conditions of the actuator based on the resonance frequencies, and conducting control, wherein the controlling step includes setting a target amplitude of the scan pattern and setting a drive frequency and drive voltages such that the scan pattern detected in the scan-pattern detecting step is within a predetermined range with respect to the target amplitude and such that conditional expressions below are satisfied:

when fx>fy, $$fd<fy \text{ and } Vx \geq Vy \quad (1)$$

or $$fd>fx \text{ and } Vx \leq Vy \quad (2),$$ and when fx≤fy, $$fd<fx \text{ and } Vx \leq Vy \quad (3)$$

or $$fd>fy \text{ and } Vx \geq Vy \quad (4)$$

where fd denotes the drive frequency, fx denotes the resonance frequency in the x direction, fy denotes the resonance frequency in the y direction, Vx denotes a maximum voltage with respect to a drive signal in the x direction, and Vy denotes a maximum voltage with respect to a drive signal in the y direction.

Another aspect of the present invention provides a drive-condition setting method applied to an optical scanning apparatus having a fiber and an actuator, the fiber optically guiding illumination light emitted from a light source and radiating the illumination light from its distal end onto an observation target, the actuator vibrating the distal end of the fiber with a predetermined drive frequency in two axial directions including an x direction and a y direction, the drive-condition setting method comprising: a controlling step of measuring resonance frequencies in the x direction and the y direction of the fiber, setting drive conditions based on the resonance frequencies, and conducting control, wherein the controlling step includes calculating a difference in phase shift amounts between the x direction and the y direction based on a phase shift of a vibration waveform of the fiber with respect to the x direction and a phase shift of a vibration waveform of the fiber with respect to the y direction, and setting a corrected phase difference by correcting a phase difference in the y direction relative to the x direction such that conditional expressions below are satisfied:

when fx≤fy, $$\theta'=\theta-|\Delta\theta| \quad (5),$$ and when fx>fy, $$\theta'=\theta+|\Delta\theta| \quad (6)$$

where fx denotes the resonance frequency in the x direction, fy denotes the resonance frequency in the y direction, θ' denotes the corrected phase difference, θ denotes the phase difference of a y-direction voltage waveform relative to that of the x direction, and |Δθ| denotes the difference in phase shift amounts between the x direction and the y direction.

The aforementioned aspects are advantageous in that the drive conditions of an optical scanning apparatus can be appropriately set.

REFERENCE SIGNS LIST 10 drive-condition setting device body
11 controller
12 light source unit
13 drive circuit
14 processing circuit
15 storage unit
16 illumination fiber
17 drive signal line
18 display device
19 input device
20 PSD
21 detection signal line
30 endoscope
32 insertion section
33 illumination fiber
33a distal end
34 actuator

The invention claimed is:

1. A drive-condition setting device applied to an optical scanning apparatus having a fiber and an actuator, the fiber being configured to optically guide illumination light emitted from a light source and radiate the illumination light from its distal end onto an observation target, the actuator being configured to vibrate the distal end of the fiber with a predetermined drive frequency in two axial directions including an x direction and a y direction, the drive-condition setting device comprising:

a controller configured to:
   receive a detected scan pattern of the illumination light output from the distal end of the fiber; and
   measure resonance frequencies in the x direction and the y direction of the fiber and set drive conditions of the actuator based on the resonance frequencies and conduct control,
   wherein the controller sets a target amplitude of the scan pattern and sets a drive frequency and drive voltages such that the detected scan pattern is within a predetermined range with respect to the target amplitude and such that conditional expressions below are satisfied:

when fx>fy, $$fd<fy \text{ and } Vx \geq Vy$$

or $$fd>fx \text{ and } Vx \leq Vy,$$ and when fx≤fy, $$fd<fx \text{ and } Vx \leq Vy$$

or $$fd>fy \text{ and } Vx \geq Vy$$

where fd denotes the drive frequency, fx denotes the resonance frequency in the x direction, fy denotes the resonance frequency in the y direction, Vx denotes a maximum voltage with respect to a drive signal in the x direction, and Vy denotes a maximum voltage with respect to a drive signal in the y direction; and wherein the controller firstly sets the drive frequency and the drive voltage for a direction in which a voltage value becomes relatively higher between the drive voltage for the x direction and the drive voltage for the y direction, and subsequently sets the drive voltage for a direction in which the voltage value becomes low.

2. A drive-condition setting device applied to an optical scanning apparatus having a fiber and an actuator, the fiber being configured to optically guide illumination light emitted from a light source and radiate the illumination light from its distal end onto an observation target, the actuator being configured to vibrate the distal end of the fiber with a predetermined drive frequency in two axial directions including an x direction and a y direction, the drive-condition setting device comprising:
  a controller configured to measure resonance frequencies in the x direction and the y direction of the fiber and set drive conditions based on the resonance frequencies and conduct control,
  wherein the controller calculates a difference in phase shift amounts between the x direction and the y direction based on a phase shift of a vibration waveform of the fiber with respect to the x direction and a phase shift of a vibration waveform of the fiber with respect to the y direction, and sets a corrected phase difference by correcting a phase difference in the y direction relative to the x direction such that conditional expressions below are satisfied:
when fx≤fy, $$\theta'=|\Delta\theta|, \text{ and}$$

when fx>fy, $$\theta'=|\Delta\theta|$$

where fx denotes the resonance frequency in the x direction, fy denotes the resonance frequency in the y direction, θ' denotes the corrected phase difference, θ denotes the phase difference of a y-direction voltage waveform relative to that of the x direction, and |Δθ| denotes the difference in phase shift amounts between the x direction and the y direction.

3. A drive-condition setting method applied to an optical scanning apparatus having a fiber and an actuator, the fiber being configured to optically guide illumination light emitted from a light source and radiate the illumination light from its distal end onto an observation target, the actuator being configured to vibrate the distal end of the fiber with a predetermined drive frequency in two axial directions including an x direction and a y direction, the drive-condition setting method comprising:
  controlling by measuring resonance frequencies in the x direction and the y direction of the fiber, setting drive conditions based on the resonance frequencies, and conducting control,
  wherein the controlling includes calculating a difference in phase shift amounts between the x direction and the y direction based on a phase shift of a vibration waveform of the fiber with respect to the x direction and a phase shift of a vibration waveform of the fiber with respect to the y direction, and setting a corrected phase difference by correcting a phase difference in the y direction relative to the x direction such that conditional expressions below are satisfied:
when fx≤fy, $$\theta'=|\Delta\theta| \quad (5), \text{ and}$$

when fx>fy, $$\theta'=\theta+|\Delta\theta| \quad (6)$$

where fx denotes the resonance frequency in the x direction, fy denotes the resonance frequency in the y direction, θ' denotes the corrected phase difference, θ denotes the phase difference of a y-direction voltage waveform relative to that of the x direction, and |Δθ| denotes the difference in phase shift amounts between the x direction and the y direction.

\* \* \* \* \*